(12) United States Patent
Maskara et al.

(10) Patent No.: US 8,417,336 B2
(45) Date of Patent: Apr. 9, 2013

(54) SYSTEM AND METHOD FOR PACING RATE CONTROL UTILIZING PATIENT HEMODYNAMIC STATUS INFORMATION

(75) Inventors: Barun Maskara, Blaine, MN (US); Lili Liu, Maple Grove, MN (US); Guy Alvarez, Lino Lakes, MN (US); Scott A. Meyer, Lakeville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 26 days.

(21) Appl. No.: 12/787,868

(22) Filed: May 26, 2010

(65) Prior Publication Data
US 2010/0305650 A1    Dec. 2, 2010

Related U.S. Application Data

(60) Provisional application No. 61/182,896, filed on Jun. 1, 2009.

(51) Int. Cl.
*A61N 1/08* (2006.01)
(52) U.S. Cl. .................. 607/9; 607/11; 607/17
(58) Field of Classification Search ............... 607/9, 11, 607/17
See application file for complete search history.

(56) References Cited

U.S. PATENT DOCUMENTS

| | | | |
|---|---|---|---|
| 4,686,987 A | 8/1987 | Salo et al. |
| 4,708,143 A | 11/1987 | Schroeppel |
| 4,967,755 A | 11/1990 | Pohndorf |
| 5,129,394 A | 7/1992 | Mehra |
| 5,156,147 A | 10/1992 | Warren et al. |
| 5,324,326 A | 6/1994 | Lubin |
| 5,356,883 A | 10/1994 | Kuo et al. |
| 5,464,434 A | 11/1995 | Alt |
| 5,480,412 A | 1/1996 | Mouchawar et al. |
| 5,626,623 A | 5/1997 | Kieval et al. |
| 6,026,324 A | 2/2000 | Carlson |
| 6,119,040 A | 9/2000 | Chirife |
| 6,277,078 B1 | 8/2001 | Porat et al. |
| 6,278,894 B1 | 8/2001 | Salo et al. |
| 6,366,811 B1 | 4/2002 | Carlson et al. |
| 6,580,946 B2 | 6/2003 | Struble |

(Continued)

FOREIGN PATENT DOCUMENTS

| | | |
|---|---|---|
| EP | 0498533 | 8/1992 |
| WO | WO 2001013792 | 3/2001 |
| WO | WO 2007/099533 | 9/2007 |
| WO | WO 2007/115188 | 10/2007 |

OTHER PUBLICATIONS

International Search Report and Written Opinion issued in PCT/US2010/036137, mailed Oct. 28, 2010, 16 pages.
U.S. Appl. No. 12/787,630, filed May 26, 2010 to Maskara, Barun et al.

(Continued)

*Primary Examiner* — Joseph Dietrich
(74) *Attorney, Agent, or Firm* — Faegre Baker Daniels LLP

(57) ABSTRACT

A system and method for pacing rate control in a cardiac rhythm management (CRM) system. The method includes acquiring a pressure signal representative of coronary venous pressure (CVP) from a pressure sensor implanted within a coronary vein of the patient and generating a CVP waveform from the pressure signal. A pacing stimulus is applied to the patient's heart, and the pacing rate is increased in response to increases in patient's metabolic demand. The CVP index is monitored during the pacing rate increase, and the CRM system detects a reduction in the patient's hemodynamic performance based on the CVP index and establishes a maximum rate setting based on the pacing rate corresponding to the reduction in the patient's hemodynamic performance.

13 Claims, 7 Drawing Sheets

U.S. PATENT DOCUMENTS

| | | |
|---|---|---|
| 6,666,826 B2 | 12/2003 | Salo et al. |
| 6,839,593 B1 | 1/2005 | Sun et al. |
| 6,892,095 B2 | 5/2005 | Salo |
| 6,934,586 B2 | 8/2005 | Struble et al. |
| 6,944,499 B2 | 9/2005 | Tang et al. |
| 6,945,939 B2 | 9/2005 | Turcott |
| 6,970,742 B2 | 11/2005 | Mann et al. |
| 7,062,323 B2 | 6/2006 | Carlson et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,206,637 B2 | 4/2007 | Salo |
| 7,233,821 B2 | 6/2007 | Hettrick et al. |
| 7,269,460 B2 | 9/2007 | Chinchoy |
| 7,272,443 B2 | 9/2007 | Min et al. |
| 7,389,142 B2 | 6/2008 | Holmstrom |
| 7,409,244 B2 | 8/2008 | Salo et al. |
| 7,457,663 B2 | 11/2008 | Kalgren et al. |
| 2001/0010009 A1 | 7/2001 | Bakels et al. |
| 2002/0188329 A1 | 12/2002 | Struble |
| 2003/0074029 A1 | 4/2003 | Deno et al. |
| 2003/0130581 A1 | 7/2003 | Salo et al. |
| 2003/0181938 A1 | 9/2003 | Roth et al. |
| 2003/0204209 A1 | 10/2003 | Burnes et al. |
| 2004/0138571 A1 | 7/2004 | Salo et al. |
| 2004/0230131 A1 | 11/2004 | Kassab et al. |
| 2005/0137635 A1 | 6/2005 | Molin |
| 2006/0089679 A1 | 4/2006 | Zhu et al. |
| 2006/0247702 A1 | 11/2006 | Stegemann et al. |
| 2006/0271121 A1 | 11/2006 | Ding et al. |
| 2006/0276849 A1 | 12/2006 | Carlson et al. |
| 2006/0293714 A1 | 12/2006 | Salo et al. |
| 2007/0088221 A1 | 4/2007 | Stahmann |
| 2007/0112388 A1 | 5/2007 | Salo |
| 2007/0142732 A1 | 6/2007 | Brockway et al. |
| 2007/0149890 A1 | 6/2007 | Li et al. |
| 2007/0239218 A1 | 10/2007 | Carlson et al. |
| 2007/0239219 A1 | 10/2007 | Salo et al. |
| 2007/0249945 A1 | 10/2007 | Li et al. |
| 2008/0082135 A1 | 4/2008 | Arcot-Krishnamurthy et al. |
| 2008/0281367 A1 | 11/2008 | Zhang et al. |
| 2009/0149766 A1 | 6/2009 | Shuros et al. |
| 2009/0204163 A1 | 8/2009 | Shuros et al. |
| 2010/0042175 A1 | 2/2010 | Liu et al. |
| 2010/0305635 A1 | 12/2010 | Liu et al. |
| 2010/0305649 A1 | 12/2010 | Maskara et al. |

OTHER PUBLICATIONS

Benchimol, Alberto et al., "Hemodynamic consequences of atrial and ventricular pacing in patients with normal and abnormal hearts", American Journal of Medicine, vol. 39, No. 6, Dec. 1, 1965, 911-922.

International Search Report and Written Opinion issued in PCT/US2010/036174, mailed Jul. 21, 2010, 15 pages.

International Search Report and Written Opinion issued in PCT/US2010/035949, dated Oct. 26, 2010, 18 pages.

International Search Report and Written Opinion issued in PCT/US2010/036137, mailed Oct. 28, 2010.

International Search Report and Written Opinion issued in PCT/US2008/080778, dated Feb. 12, 2009.

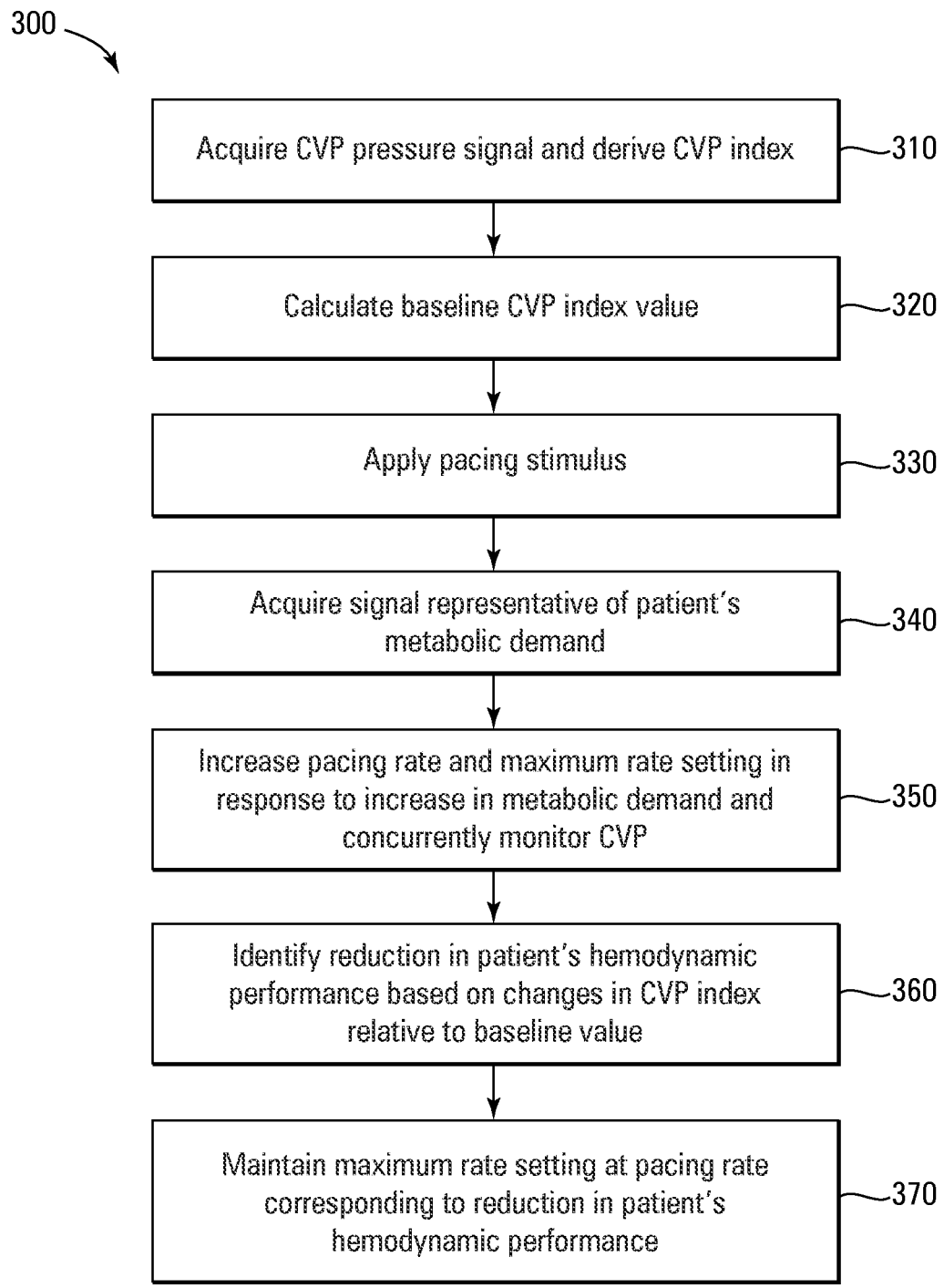

SYSTEM AND METHOD FOR PACING RATE CONTROL UTILIZING PATIENT HEMODYNAMIC STATUS INFORMATION

CROSS-REFERENCE TO RELATED APPLICATIONS

This application claims the benefit under 35 U.S.C. §119 of U.S. Provisional Application No. 61/182,896, filed Jun. 1, 2009, entitled "System and Method for Pacing Rate Control Utilizing Patient Hemodynamic Status Information," which is incorporated herein by reference for all purposes.

This application is also related to co-pending and commonly assigned U.S. Patent Publication No. 2010/0305649, filed on May 26, 2010, and entitled "System and Method for Decompensation Detection and Treatment Based on Patient Hemodynamics," which is incorporated herein by reference for all purposes.

TECHNICAL FIELD

The present invention relates to medical devices and methods for cardiac rhythm management. More specifically, the present invention relates to systems and methods for automatically adjusting the operating parameters of a cardiac rhythm management system.

BACKGROUND

Implantable cardiac rhythm management (CRM) systems, including pacemakers, implantable cardioverter/defibrillators (ICDs), and cardiac resynchronization therapy (CRT, CRT-D) devices have been used to deliver effective treatment to patients with serious cardiac arrhythmias. In particular, rate adaptive pacing systems are known which utilize data obtained from various implantable sensors, e.g., activity sensors such as accelerometers and minute ventilation sensors, to adjust pacing parameters in response to increased patient demand. Despite significant technological advances in rate adaptive pacing technologies in recent years, there exists a continuing need for improved pacing systems and methods, particularly for use in patients suffering from congestive heart failure (CHF).

SUMMARY

The present invention, in one embodiment, is a method of operating an implanted rate adaptive cardiac rhythm management system in a patient. The method comprises acquiring a pressure signal representative of coronary venous pressure (CVP) from a pressure sensor implanted within a coronary vein of the patient and generating a CVP waveform from the pressure signal, and applying a pacing stimulus to the patient's heart, the pacing stimulus being defined by a set of pacing parameters including a pacing rate. The method further comprises acquiring a signal representative of the patient's metabolic demand from at least one implanted sensor, and monitoring a CVP index derived from the CVP waveform while increasing the pacing rate in response to an increase in the patient's metabolic demand. Additionally, the method comprises detecting a reduction in the patient's hemodynamic performance based on the CVP index resulting from increasing the pacing rate and establishing a maximum rate setting based on the pacing rate corresponding to the reduction in the patient's hemodynamic performance, wherein the maximum rate setting delimits further metabolic demand-induced pacing rate increases.

In another embodiment, the present invention is a method of operating an implanted cardiac rhythm management system in a patient. The method comprises acquiring a pressure signal indicative of coronary venous pressure (CVP) from a pressure sensor implanted within a coronary vein of the patient and deriving a selected CVP index from the pressure signal, and calculating a baseline CVP index value. The method further comprises applying a pacing stimulus to the patient's heart, the pacing stimulus defined by a set of pacing parameters including a maximum rate setting, and acquiring a signal representative of the patient's metabolic demand from at least one implanted sensor. Additionally, the method comprises, responsive to an increase in the patient's metabolic demand, increasing the pacing rate and the maximum rate setting while monitoring the CVP index. The method further comprises detecting a reduction in the patient's hemodynamic performance based on a change, relative to the CVP index baseline value, in the CVP index resulting from increasing the pacing rate and maintaining the maximum rate setting at a pacing rate below the pacing rate corresponding to the detected reduction in the patient's hemodynamic performance.

In yet another embodiment, the present invention is an implantable rate adaptive cardiac rhythm management system configured for applying pacing stimuli to a patient's heart, the pacing stimuli defined by pacing parameters including a pacing rate and a maximum rate setting. The system comprises a plurality of implantable medical electrical leads configured to sense cardiac electrical activity and to deliver the pacing stimuli. At least one of the leads is configured for chronic implantation within a coronary vein of the patient's heart and includes a pressure sensor configured to generate a coronary venous pressure (CVP) signal indicative of fluid pressure within the coronary vein. The system further comprises an implantable pulse generator operatively coupled to the leads configured to generate the pacing stimuli. The pulse generator includes a control system configured to generate a CVP waveform based on the pressure signal and derive a CVP index therefrom, and detect reductions in the patient's hemodynamic performance based on the CVP index caused by an increase in the pacing rate. The control system is further configured to adaptively adjust the pacing rate and the maximum rate setting in response to changes in the patient's metabolic demand. During use, the maximum rate setting is selectively defined by the control system based on the pacing rate corresponding to the identified reduction in the patient's hemodynamic performance.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 7 is a flow chart illustrating a method of controlling pacing parameters for the CRM system of FIG. 1 according to another embodiment of the present invention.

Figure 1:
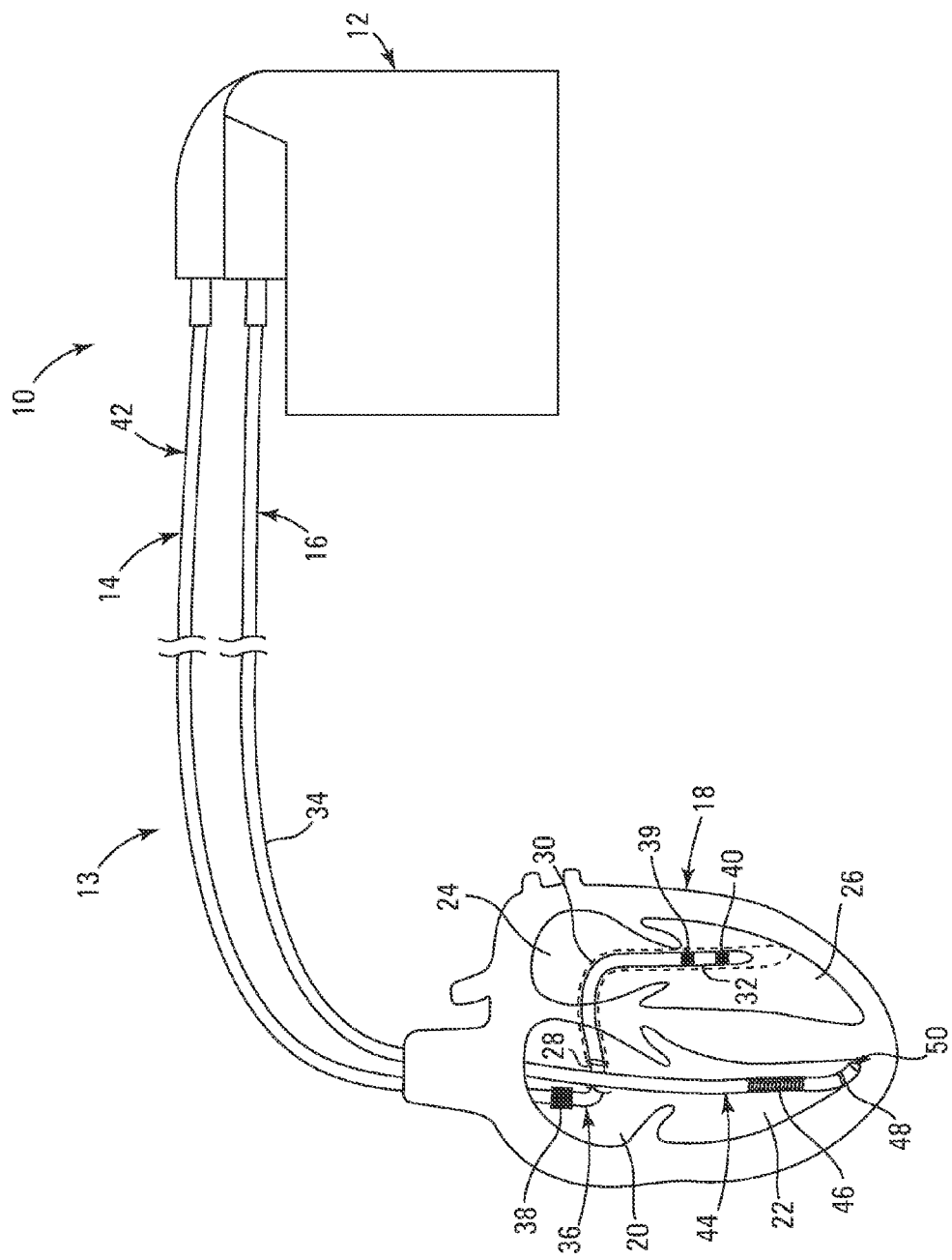
FIG. 1 is a schematic illustration of an implantable cardiac rhythm management (CRM) system according to one embodiment of the present invention in a deployed configuration.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of an implantable cardiac rhythm management (CRM) system 10 according to one embodiment of the present invention, shown in a deployed state. As shown in FIG. 1, the CRM system 10 includes a pulse generator 12 coupled to a cardiac lead system 13 including a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30. As discussed in detail below, the CRM system 10 is configured to treat cardiac arrhythmias in a patient suffering from CHF. More specifically, the CRM system 10 is a rate adaptive pacing system configured to adjust the pacing rate in response to changes in the patient's sensed metabolic demand, and utilizes hemodynamic performance information based on the output from implanted pressure sensors to further optimize the pacing system parameters. In various embodiments, the pressure sensors provide information that is indicative of or correlates closely to the patient's left ventricular pressure (LVP), which is a useful measure as an indicator of cardiac function in patients suffering from CHF.

As shown in FIG. 1, the lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes pressure sensors 38, 39, and an electrode 40. As shown, the pressure sensor 39 and the electrode 40 are positioned on the lead 14 such that, when implanted, they are both located within the branch vessel 32. As further shown, the pressures sensor 38 is positioned on the lead 14 such that, when implanted, it is located within the right atrium 20. The illustrated position of the lead 14 may be used for delivering a pacing and/or defibrillation stimulus to the left side of the heart 18. Additionally, the lead 14 may also be partially deployed in other regions of the coronary venous system, such as in the great cardiac vein or other branch vessels for providing therapy to the left side or right side of the heart 18.

In the illustrated embodiment, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown, in the illustrated embodiment, the lead 16 includes a proximal portion 34 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. The high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

In various embodiments, the lead 16 includes additional defibrillation/cardioversion and/or additional pace/sense electrodes positioned along the lead 16 so as to provide multi-polar defibrillation/cardioversion capabilities. In one exemplary embodiment, the lead 16 includes a proximal high voltage electrode in addition to the electrode 46 positioned along the lead 16 such that it is located in the right atrium 20 (and/or superior vena cava) when implanted. Additional electrode configurations can be utilized with the lead 16. In short, any electrode configuration can be employed in the lead 16 without departing from the intended scope of the present invention.

In various embodiments, the lead 14 can be configured according to the various embodiments described in co-pending and commonly assigned U.S. Provisional Patent Application 61/088,270 titled "Implantable Lead and Coronary Venous Pressure Sensor Apparatus and Method" to Liu, et al. or commonly assigned U.S. Pat. No. 7,409,244 titled "Method and Apparatus for Adjusting Interventricular Delay Based on Ventricular Pressure," to Salo, et al., the disclosures of which are incorporated herein by reference in their entireties. In other embodiments, the lead 14 with pressure sensor 39 and/or 38 can have other suitable configurations.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient suitable for treating cardiac tachyarrhythmias. In various embodiments, the pulse generator 12 is a pacemaker, an implantable cardioverter defibrillator (ICD) or a cardiac resynchronization (CRT) device configured for bi-ventricular pacing and including defibrillation capabilities (i.e., a CRT-D device). While not shown in FIG. 1, the pulse generator 12 includes hardware, software, and circuitry operable as a detection/energy delivery system configured to receive cardiac rhythm signals from the lead electrode(s) 40, 48, 50 and pressure signals from the pressure sensor(s) 38, 39, and also to deliver a therapeutic electrical stimulus to the electrodes 40, 48, 50.

In various embodiments, the CRM system 10 further includes an additional lead deployed in the right atrium 20, which lead may include one or more additional electrodes sensing intrinsic cardiac signals and/or delivering electrical stimuli to the cardiac tissue within the right atrium 20.

The pressure sensor 39 is operable to sense and to generate an electrical signal representative of a fluid pressure parameter within the coronary vein 32 in which it is implanted. The pressure sensor 39 can be any device, whether now known or later developed, suitable for sensing pressure parameters within the coronary venous system and generating and transmitting a signal indicative of such pressure parameters to another device, e.g., the pulse generator 12. In various embodiments, the pressure sensor 39 is configured to sense and generate a signal indicative of hydrostatic pressure within the coronary vein. In various embodiments, the pressure sensor 39 can be a micro-electrical-mechanical system (MEMS) device, which utilizes semiconductor techniques to build microscopic mechanical structures in a substrate made from silicon or similar materials. In various embodiments, the pressure sensor 39 can include a micro-machined capacitive or piezoresistive sensor exposed to the bloodstream. Other pressure sensor technologies, such as resistive strain gages, are known in the art and can also be employed as a pressure sensor 39.

In other exemplary embodiments, the pressure sensor 39 can include one or more piezoelectric elements. Such piezoelectric elements are configured to flex and/or deflect in response to changes in pressure within the coronary vein in which it is implanted, and to generate an output current or voltage proportional to the corresponding pressure change. In such embodiments, the pressure sensor 39 may advantageously be configured to sense fluid characteristics indicative of changes in coronary venous pressure during the cardiac cycle, e.g., dp/dt, which in turn can be monitored over time.

Figure 2:
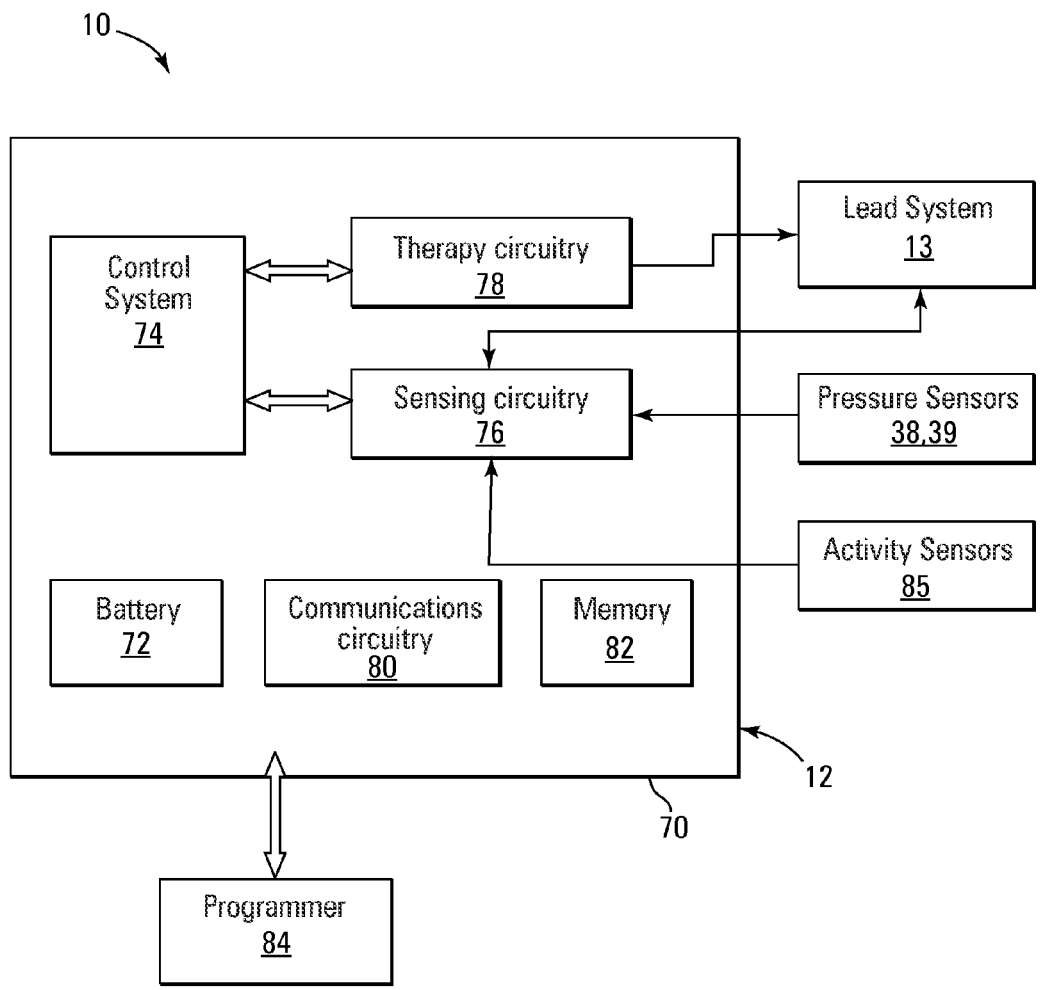
FIG. 2 is a block diagram illustrating functional components of the implantable CRM system of FIG. 1.

FIG. 2 is a schematic functional block diagram of an embodiment of the implantable medical system 10. As shown in FIG. 2, the system 10 is divided into functional blocks. The illustrated configuration is exemplary only, and there exist many possible configurations in which these functional blocks can be arranged. The example depicted in FIG. 2 is one possible functional arrangement. The system 10 includes circuitry for receiving cardiac electrical signals, coronary venous pressure signals, and in some embodiments, right atrial pressure signals from the heart 18 and generating and delivering electrical energy in the form of pace pulses or cardioversion/defibrillation pulses to the heart 18.

As discussed above, the cardiac lead system 13, which includes the leads 14, 16 may be implanted so that the cardiac electrodes 40, 48, 50 (see FIG. 1) contact heart tissue. The cardiac electrodes of the lead system 13 sense cardiac signals associated with electrical activity of the heart. In addition, the pressure sensors 38, 39 on the lead 14 detect and generate pressure signals indicative of blood pressure within the right atrium 20 and coronary vein 32, respectively. The sensed cardiac signals and pressure signals are transmitted to a the pulse generator 12 through the lead system 13. The cardiac electrodes and lead system 13 may be used to deliver electrical stimulation generated by the pulse generator 12 to the heart to mitigate various cardiac arrhythmias. The pulse generator 12, in combination with the cardiac electrodes and the lead system 13, may detect cardiac signals and deliver therapeutic electrical stimulation to any of the left and right ventricles and left and right atria, for example.

As shown, the pulse generator 12 includes circuitry encased in a hermetically sealed housing 70 suitable for implanting in a human body. Power is supplied by a battery 72 that is housed within the housing 70. In one embodiment, the pulse generator circuitry is a programmable microprocessor-based system, including a control system 74, sensing circuitry 76, therapy circuitry 78, communications circuitry 80, and memory 82. The memory 82 may be used, for example, to store programmed instructions for various pacing and defibrillation therapy and sensing modes, and also data associated with sensed cardiac signals or other physiologic data, e.g., blood pressure. The parameters and data stored in the memory 82 may be used on-board for various purposes and/or transmitted via telemetry to an external programmer unit 84 or other patient-external device, as desired. In various embodiments, the stored data can be uploaded by a clinician and/or transmitted over an advanced patient management (APM) system, such as the LATITUDE® system marketed by Boston Scientific Corporation.

The communications circuitry 80 allows the pulse generator 12 to communicate with the external programmer unit 84 and/or other patient-external system(s). In one embodiment, the communications circuitry 80 and the programmer unit 84 use a wire loop antenna and a radio frequency telemetric link to receive and transmit signals and data between the programmer 84 and communications circuitry 80. In this manner, programming commands may be transferred to the pulse generator 12 from the programmer 84 during and after implantation. In addition, stored cardiac data may be transferred to the programmer unit 84 from the pulse generator 12, for example.

The sensing circuitry 76 detects cardiac signals sensed at the cardiac electrodes 40, 48, 50, as well as blood pressure signals generated by the pressure sensors 38, 39, and signals indicative of patient activity from implanted activity sensors 85, which provide information relating to the patient's metabolic demand. The sensing circuitry 76 may include, for example, amplifiers, filters, A/D converters and other signal processing circuitry. Cardiac signals and pressure signals processed by the sensing circuitry may be communicated to the control system 74.

The therapy circuitry 78 is controlled by the control system 74 and may be used to deliver therapeutic stimulation pulses to the heart through one or more of the cardiac electrodes, according to a pre-established pacing regimen under appropriate conditions. Thus, in various embodiments, the therapy circuitry 78 is configured to deliver pacing stimuli to the right side and, in the case of a CRT or CRT-D system such as the CRM system 10, also to the left side of the heart 18. In various embodiments, the therapy circuitry 78 is also configured to deliver anti-tachycardia therapy stimuli to the ventricles and/or the atria. Such therapies may include, without limitation, relatively low-energy anti-tachycardia pacing pulses as well as high-energy shocks to treat and disrupt ventricular fibrillation episodes.

The control system 74 is used to control various subsystems of the pulse generator 12, including the therapy circuitry 78 and the sensing circuitry 76. The control system 74 perform various functions, including, for example, arrhythmia analysis and therapy selection. An arrhythmia analysis section of the control system 74 may compare signals detected through the sensing circuitry 76 to detect or predict various cardiac arrhythmias, and to assist selection of appropriate therapies for the patient.

The control system 74 is also configured to adaptively adjust pacing parameters in response to changes in the patient's metabolic demand due, for example, to changes in the patient's physical activity. In this regard, the control system 74 analyzes signals from the patient activity sensors 85 to determine whether pacing parameters, in particular, the pacing rate, should be increased or decreased in response to increases or decreases, respectively, in the patient's metabolic demand. As explained in detail below, according to various embodiments of the present invention, the control system 74 is also configured to utilize pressure signals from the pressure sensors 38, 39 in adjusting pacing rates based on increases in the patient's metabolic demand.

As discussed above, LVP is a useful indicator of hemodynamic performance in patients with CHF. In particular, LVP can provide an indication as to worsening hemodynamic conditions, including a decrease in cardiac output (CO), as a result of an increase in the patient's heart rate.

Figure 3:
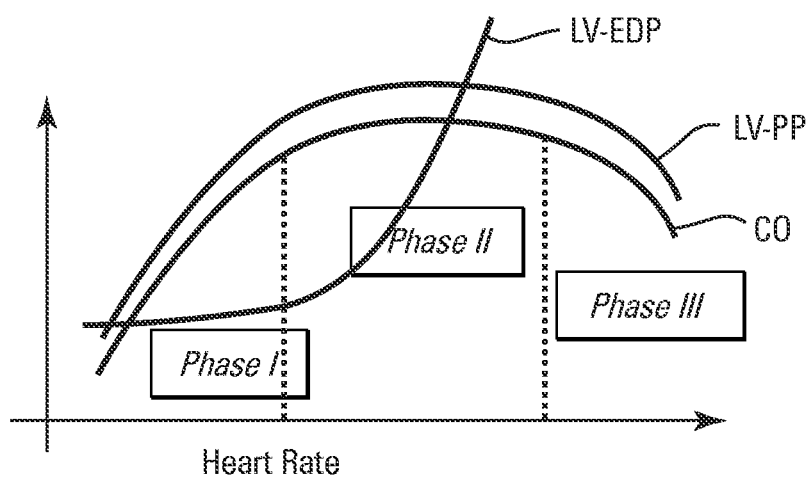
FIG. 3 is a chart schematically depicting cardiac output and selected hemodynamic performance indicators as a function of heart rate.

FIG. 3 is a schematic graphical illustration showing cardiac output (CO) and two LVP parameters—LV pulse pressure (LV-PP) and LV end diastolic pressure (LV-EDP)—as a function of increasing heart rate. As shown in FIG. 3, a patient's (particularly CHF patient's) response to increasing heart rate, whether intrinsically driven or paced or both, typically has a bimodal response. That is, as shown in FIG. 3, CO generally increases initially with increasing heart rate (Phase I in FIG. 3), then plateaus (Phase II), and then begins to decrease (Phase III). Thus, while it is desirable to increase heart rate, e.g., by increasing a pacing rate, to match an increase in metabolic demand due to an increase in patient activity, it is also desirable to avoid driving the patient's heart into the zone in FIG. 3 indicated by decreasing CO. As such, rate adaptive pacing protocols generally include one or more maximum rate settings to limit the maximum allowable pacing rate so as to avoid adversely impacting CO in situations where the patient's metabolic demand would otherwise dictate further increases in the pacing rate.

Two such maximum rate settings are the maximum sensor rate (MSR) and the maximum tracking rate (MTR). As is generally known, MSR and MTR are closely related, but not identical, pacing parameters. That is, MSR is the maximum pacing rate allowed as a result of sensor control (e.g., from an accelerometer or other activity sensor input), while MTR is the maximum ventricular paced rate that is allowed in response to sensed atrial rhythms. In either case, pacing above the MSR or MTR limit the maximum pacing rate in response to sensed events.

In conventional pacing systems lacking direct hemodynamic status information inputs, the MSR/MTR are generally programmed by the clinician based on empirical information regarding the patient. Often the clinician will set these parameters well below the range at which hemodynamic compromise would be expected to occur due to increased pacing rates. As a result, the pacing rate may be unnecessarily limited in situations where the patient's metabolic demand would otherwise call for an increase in the pacing rate and the patient's hemodynamic status is not materially compromised due to the increased rate.

Thus, in an embodiment of the present invention, the CRM system 10 utilizes hemodynamic performance information to adaptively adjust the MSR and/or MTR so as to accommodate increases in the patient's metabolic demand.

As discussed above, FIG. 3 also illustrates changes in exemplary LVP parameters—LV pulse pressure (LV-PP) and LV end diastolic pressure (LV-EDP)—as a function of increasing heart rate. As shown in FIG. 3, increases in heart rate also affect the LV-PP and LV-EDP. In particular, the shape of the LV-PP curve generally tracks the shape of the CO curve as the patient's heart rate increases, such that the LV-PP initially increases with increasing heart rate, then plateaus, and subsequently begins to decline as the heart rate further increases. Additionally, as further shown in FIG. 3, the LV-EDP is initially relatively constant as the heart rate increases, then rises relatively sharply. Thus, information indicative of the patient's LV-PP and/or LV-EDP can be utilized by the CRM system 10 to adaptively adjust the MSR/MTR to optimize rate adaptive pacing in response to patient metabolic demand increases.

For example, an LV-PP waveform such as shown in FIG. 3 can provide an indication as to when the patient's hemodynamic status begins to worsen as a result of an increase in pacing/heart rate. That is, a decrease in LV-PP accompanying an increase in pacing rate can indicate a corresponding decrease in CO, and further pacing rate increases, even as metabolic demand continues to increase, can be avoided. Similarly, an LV-EDP waveform such as shown in FIG. 3 can also be generated and the slope of this waveform can be determined. As is apparent from FIG. 3, an increase in the slope of the LV-EDP curve can be used to limit further increases in pacing rate. Alternatively, a change in the average LV-EDP value during the rate increase relative to a baseline LV-EDP value (derived prior to the start of the rate increase) can be calculated and monitored. Accordingly, the pacing rate can be limited where the relative change in average LV-EDP compared to the baseline value exceeds a threshold value, LV-PP and LV-EDP are only illustrative of the LV pressure parameters that can be estimated to assess the patient's hemodynamic status. Other exemplary parameters include, without limitation, LV systolic pressure (LV-SP), mean LVP, and LV dp/dt.

Figure 4:
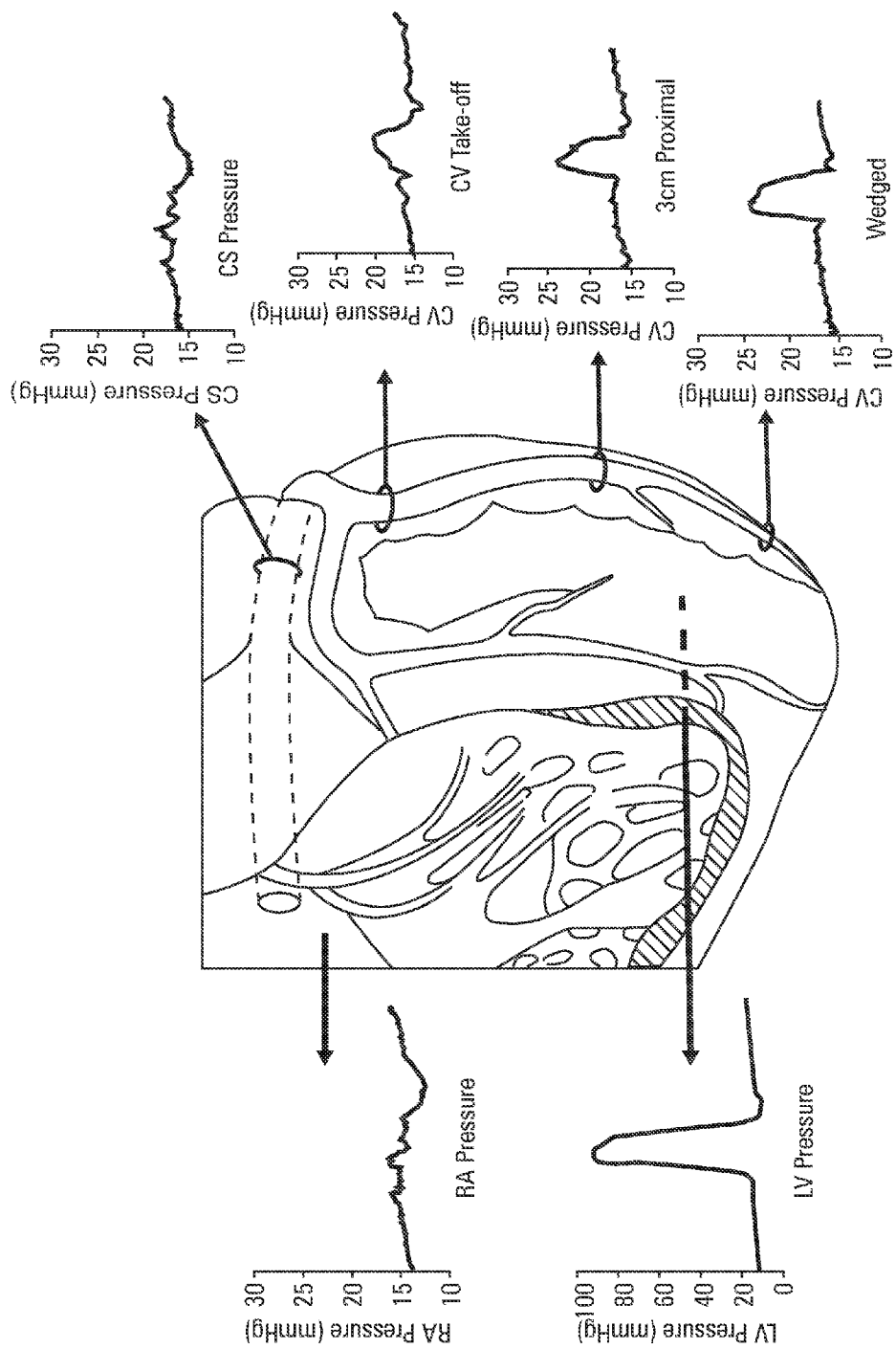
FIG. 4 is an illustration of coronary venous system pressure waveforms that can be obtained utilizing the CRM system of FIG. 1.

However, obtaining direct LV pressure information chronically is both technically and clinically challenging. Accordingly, in various embodiments, as described in detail below, coronary venous pressure (CVP) is utilized as a surrogate for direct LVP measurement. As explained above, the pressure sensors 38, 39 are configured to detect and generate pressure signals representative of fluid pressure within the right atrium 20 and the coronary vein 36, respectively. From these pressure signals, pressure waveforms can be derived and evaluated by the sensing circuitry 76 and the control system of the pulse generator 12. FIG. 4 illustrates pressure waveforms obtained from the right atrium (RA), left ventricle (LV), coronary sinus (CS) and various locations in a coronary vein (CV) in an exemplary animal study. As shown, the coronary venous pressure (CVP) waveform takes on the same general shape as the LV waveform, particularly where the CVP is taken from a location lower in the coronary vein, i.e., as indicated by the "Wedged" (apical two-thirds) CV pressure graph.

Figure 5:
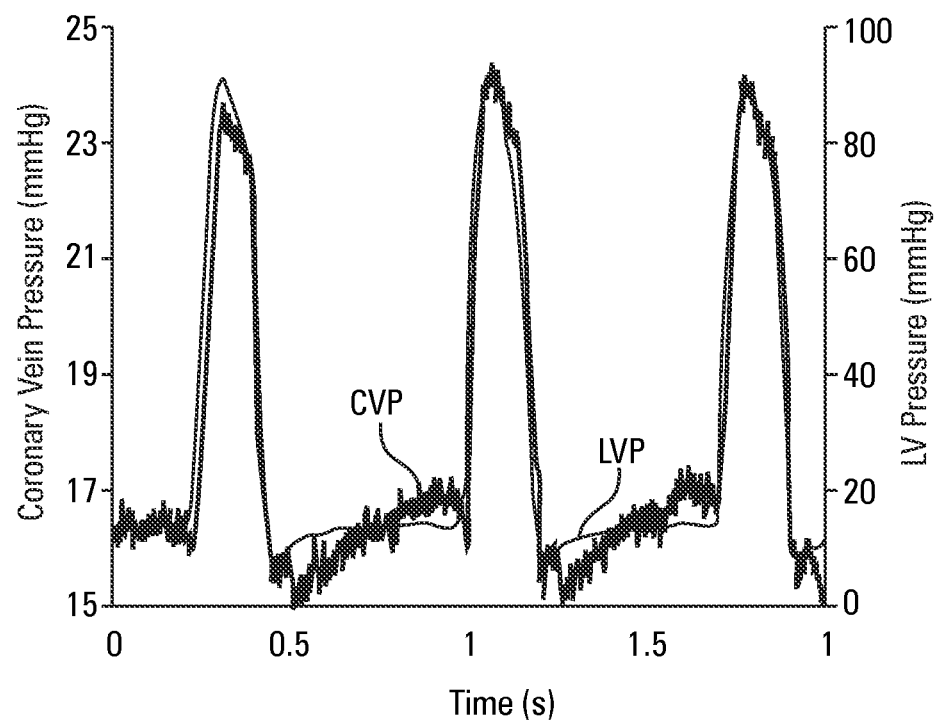
FIG. 5 is an illustration depicting a coronary venous pressure waveform and corresponding left ventricular pressure waveform.

FIG. 5 is an illustration depicting a CVP waveform and a corresponding LVP waveform also obtained in an exemplary animal study. As can be seen in FIG. 5, the CVP and LVP waveforms correlate closely to one another. Thus, in view of the close correlation between coronary venous pressure and LV pressure, CVP can function as a surrogate for LVP in the CRM system 10, which can then derive one or more CVP indexes that closely correlate to corresponding LVP indexes, and can thus be utilized in the same manner as the LVP indexes to adaptively adjust maximum pacing rate settings, e.g., MSR/MTR, in response to changes in the patient's metabolic demand.

Thus, in one embodiment, an exemplary CVP index used by the CRM system 10 is based on CVP pulse pressure (CVP-PP), which as will be apparent in view of FIGS. 4 and 5 and the corresponding discussion, will correlate closely to LVP-PP. In this case, the control system 74 can generate a CVP waveform based on the pressure signal obtained from the pressure sensor 39, and from this waveform can derive a secondary waveform tracking CV-PP over time. From this, an appropriate CVP index, such as an average CV-PP value over a specified interval, or a direct CV-PP value itself, can be monitored by the control system 74 for establishing pacing rate settings. Similarly, coronary venous end diastolic pressure (CV-EDP) will also correlate closely to LV-EDP, and thus the CVP index can also be based on CV-EDP and utilized by the control system 74 to establish maximum pacing rate settings.

Figure 6:
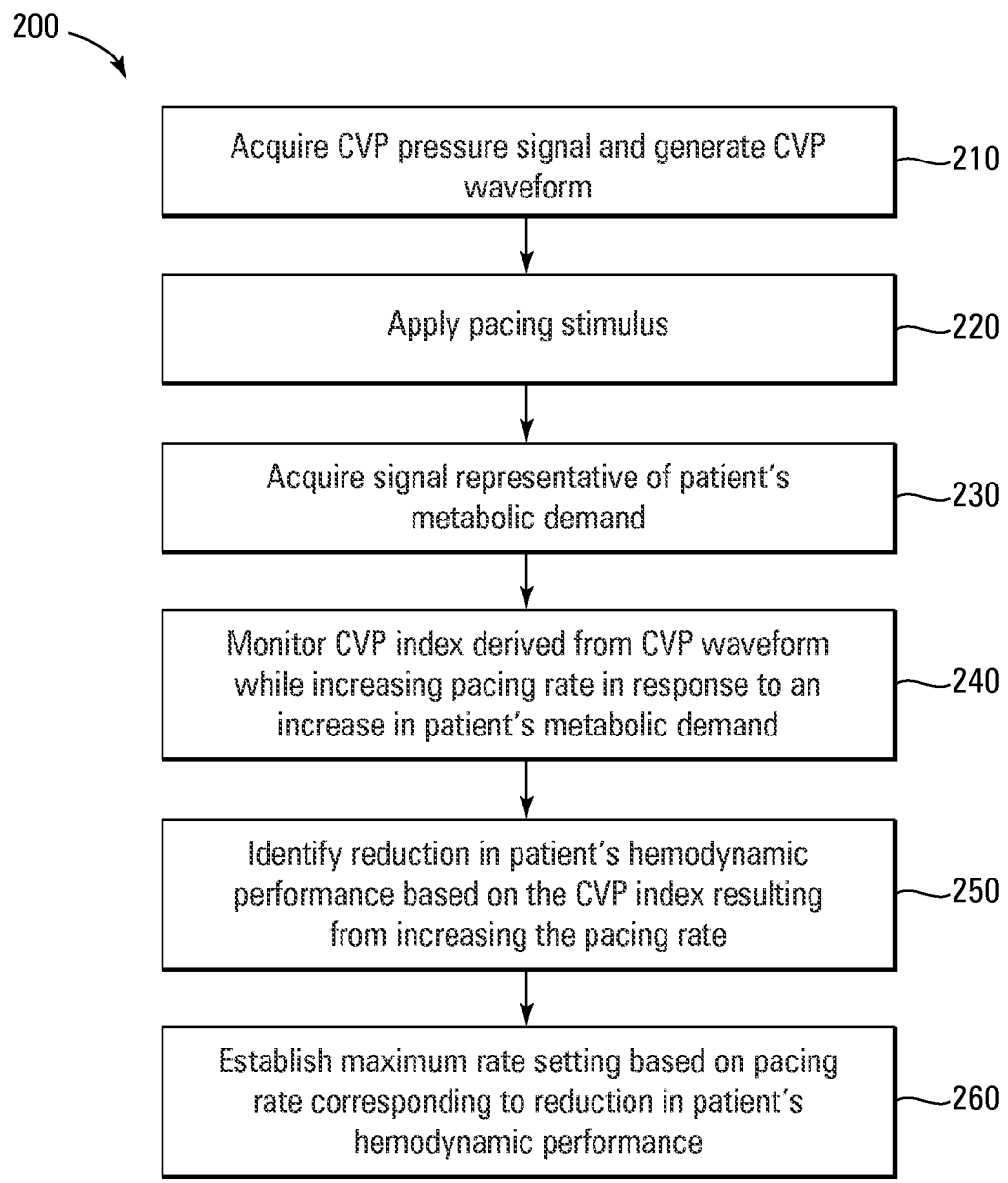
FIG. 6 is a flow chart illustrating an exemplary method of controlling pacing settings for the CRM system of FIG. 1 according to one embodiment of the present invention.

FIG. 6 is a flow chart illustrating one method 200 of pacing parameter control that can be accomplished by the CRM system 10 according to one embodiment of the present invention. As shown in FIG. 6, the method 200 begins with the CRM system 10 acquiring a pressure signal representative of CVP, from which the control system 74 generates a CVP waveform (block 210). As further shown in FIG. 6, the method 200 contemplates that a pacing stimulus is applied to the patient's heart by the CRM system 10 (block 220). Additionally, the CRM system acquires one or more signals representative of the patient's metabolic demand from an implanted sensor (block 230). Such sensors can include, without limitation, activity sensors such as accelerometers and minute ventilation sensors, which are well known in the art and are thus not discussed in further detail here.

As further shown in FIG. 6, the CRM system 10 monitors a CVP index (or a plurality of indexes) derived from the CVP waveform while concurrently increasing the pacing rate in response to increased metabolic demand (block 240). For example, if the patient's physical activity increases, the resulting increase in the patient's metabolic demand will be detected by the CRM system 10, which will in turn initiate an increase in the pacing rate according to a protocol programmed by the clinician.

The selected CVP index(es) can be any index correlating to an LVP parameter indicative of the patient's hemodynamic performance. That is, in various embodiments, the CVP index is based on CV-PP, CV-EDP, CV-SP, CV dp/dt, and the like. In various embodiments, the CVP index may be derived directly from the CVP waveform, e.g., as a secondary waveform based on a CV parameter such as CV-PP or CV-EDP calculated on a beat-by-beat basis, or it may itself be calculated from such values, e.g., as an average value over a selected interval (e.g., a selected number of beats, or a selected time interval).

As further shown in FIG. 6, the method 200 further includes detecting a reduction (or an impending reduction) in the patient's hemodynamic performance, based on the CVP index, as a result of the increase in the pacing rate in response to the increased metabolic demand (block 250). The control system 74 in turn establishes a maximum pacing rate setting (e.g., MSR/MTR setting) based on the pacing rate corresponding to the point at which hemodynamic performance begins to decrease. For example, in one embodiment, control system 74 is configured to define the maximum rate setting at a predetermined percentage of or below the pacing rate at which the reduction of hemodynamic performance is detected. In another embodiment, the control system 74 is configured to set the maximum rate setting at a certain number of beats/minute below the pacing rate at which the reduction of hemodynamic performance is detected. Still other criteria for establishing the maximum rate setting upon the detection of a decrease in hemodynamic performance may be employed. In all cases, the CVP data obtained from the implanted pressure sensor(s) provide a means for the control system 74 to dynamically adjust the maximum pacing rate limits for the CRM system 10 based on actual patient hemodynamic status feedback.

The particular CVP index utilized can be any CVP index providing a close correlation to a hemodynamically significant LVP parameter. For example, the control system 74 may, in one embodiment, monitor CV-PP as the pacing rate is increased in response to increased metabolic demand. Referring back to FIG. 3, because CV-PP closely correlates with LV-PP, the shape of a CV-PP waveform as a function of heart/pacing rate will take on the same general shape as the LV-PP waveform illustrated in FIG. 3. Thus, if the control system 74 detects a CV-PP waveform during a period of increasing pacing rate characterized by an initial increase in CV-PP, followed by a generally constant CV-PP and in turn by a decrease in CV-PP, the point at which the CV-PP begins to decrease will generally signify a reduction, or at least an impending reduction, in the patient's hemodynamic performance. Alternatively, the control system 74 may be configured to associate a decrease in CV-PP during a period of increasing heart rate (without regard to the preceding CV-PP behavior) as an indication of a reduction in hemodynamic performance.

In another embodiment, the CV-EDP provides the basis for the CVP index utilized by the control system 74 in the method 200. For example, the CV-EDP can be determined based on the CVP waveform (e.g., on a beat-by-beat basis, or as an average CV-EDP over a selected time interval, number of beats, etc.), and then monitored by the control system 74 as the pacing rate is increased in response to changes in metabolic demand. In one embodiment, the control system 74 generates a secondary CVP waveform as a function of time or heart/pacing rate. Referring back to FIG. 3, the control system 74 can then monitor changes in the slope of the CV-EDP waveform, whereby a substantial increase in the slope accompanying an increase in pacing rate indicates a reduction (or impending reduction) in hemodynamic performance as a result of the pacing rate increase. The CV-EDP slope increase associated with a decrease in hemodynamic performance can, for example, be a programmed value determined based on the patient's clinical history or needs.

Still other CVP indexes, e.g., based on CV dp/dt, CV-SP, etc., may be used by the control system 74 in addition to or in lieu of the CV-PP and/or CV-EDP values discussed above. FIG. 7 is a flow chart illustrating a method 300 of controlling pacing parameters of the CRM system 10 according to another embodiment of the present invention. As shown in FIG. 7, the method 300 begins with the control system 74 of the CRM system 10 acquiring a pressure signal representative of CVP and deriving a CVP index from the pressure signal (block 310). The control system 74 then calculates a baseline CVP index value (block 320). The baseline CVP index value can be calculated at any appropriate interval. In one embodiment, the baseline CVP index value is based on CVP data during a steady state operation of the CRM system prior to the initiation of a pacing rate increase in response to changes in metabolic demand. The baseline can be based on a single cycle, or alternatively, may be an average value over a preselected time interval or a predetermined number of cardiac beats.

As with the method 200 described above, the method 300 further contemplates that a pacing stimulus is applied to the patient's heart by the CRM system 10 (block 330). In one embodiment, pacing parameters for the pacing stimulus include a pacing rate and a maximum rate setting (e.g., MSR and/or MTR). Additionally, the CRM system acquires one or more signals representative of the patient's metabolic demand from an implanted sensor, as described above (block 340).

As further shown in FIG. 7, the CRM system 10 concurrently monitors the CVP index (or a plurality of indexes) and increases the pacing rate and maximum rate setting in response to increased metabolic demand (block 350). Subsequently, the method 300 further includes detecting, based on the CVP index, a reduction (or an impending reduction) in the patient's hemodynamic performance as a result of the increase in the pacing rate in response to the increased metabolic demand (block 360). Upon detecting the reduction in hemodynamic performance, the control system 74 maintains the maximum rate setting at a pacing rate at or below (i.e., within a predefined percentage or beats/minute of) the pacing rate above which any further increase in pacing rate leads to the decrease (or impending decrease) in the patient's hemodynamic performance (block 370).

In the method 300, the CVP index corresponding to the increasing pacing rate is compared to the baseline CVP index value to detect or predict the onset of a decrease in hemodynamic function. In one embodiment, the control system 74 is configured to define a change in the CVP index value (calculated at increased pacing rates due to increased metabolic demand) relative to the baseline CVP index value that exceeds a predetermined threshold amount as an indicator of a decrease in hemodynamic function.

For example, the CVP index can be based on changes in the CV-EDP during metabolic demand-induced pacing rate increases. In this case, for example, the control system 74 will calculate a rolling average CV-EDP value during the pacing rate increase period and compare this rolling average CV-EDP to the baseline CV-EDP value calculated prior to the rate increase. If the difference between any rolling average CV-EDP value and the baseline value does not exceed a predetermined threshold amount, the control system will continue to allow the pacing rate to increase in response to further increases in metabolic demand. If, however, the difference between the rolling average CV-EDP value during the rate increase exceeds the predetermined threshold, the control system 74 will identify this situation as indicative of a reduction in CO or some other hemodynamic performance parameter, and will set the maximum rate setting accordingly.

Additional enhancements can be incorporated into either of the methods 200 or 300 described above. For example, upon establishing the maximum rates setting in response to the detection of hemodynamic performance reduction as described above, the CRM system 10 can be programmed to re-open the monitoring window, e.g., after a predetermined time period at an elevated pacing rate, to determine whether the patient's hemodynamic state has stabilized to the point where the patient can tolerate further pacing rate increases in response to continued increased metabolic demand. In addition, in various embodiments, the pressures sensor 38 (see FIG. 1) detects and generates a signal indicative of right atrial pressure and right ventricular filling pressure (RV-EDP), which can be a useful indication for right ventricular hemodynamics and can also be used by the control system 74 in conjunction with the CVP indexes discussed above for establishing the maximum pacing rate settings.

Thus, the various embodiments of the present invention provide for dynamic adjustment of pacing rate limits by the implanted CRM system 10, so as to improve the ability of the CRM system 10 to accommodate the patient's metabolic demands while substantially maintaining the patient's hemodynamic performance. The CRM system 10 thus provides operational advantages, particularly when used with patients diagnosed with CHF, where the pacing rate limits may otherwise need to be set at artificially low settings to avoid unintentionally reducing the patient's hemodynamic performance.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of operating an implanted rate adaptive cardiac rhythm management system in a patient, the method comprising:
acquiring a pressure signal representative of coronary venous pressure (CVP) from a pressure sensor implanted within the lower apical two thirds of a coronary vein of the patient and generating a CVP waveform therefrom;
applying a pacing stimulus to the patient's heart, the pacing stimulus defined by a set of pacing parameters including a pacing rate;
acquiring a signal representative of the patient's metabolic demand from at least one implanted sensor;
monitoring a CVP index derived from the CVP waveform while increasing the pacing rate in response to an increase in the patient's metabolic demand, wherein the CVP index is based on coronary venous pulse pressure (CV-PP) sensed by the pressure sensor;
detecting a reduction in the patient's hemodymanic performance based on the CVP index resulting from increasing the pacing rate; and
establishing a maximum rate setting based on the pacing rate corresponding to the reduction in the patient's hemodynamic performance, wherein the maximum rate setting delimits further metabolic demand-induced pacing rate increases.

2. The method of claim 1 wherein establishing the maximum rate setting includes defining the maximum rate setting as a pacing rate above which any further increase in pacing rate leads to the reduction in the patient's hemodynamic performance.

3. The method of claim 1 wherein establishing the maximum rate setting includes defining the maximum rate setting as a pacing rate below, by a predetermined amount, a pacing rate above which any further increase in pacing rate leads to the reduction in the patient's hemodynamic performance.

4. The method of claim 1 wherein the predetermined amount is a predetermined number of beats per minute or a predetermined percentage.

5. The method of claim 1 wherein monitoring the CVP index includes generating a waveform of average CV-PP values as a function of the pacing rate during a period in which the pacing rate is increased in response to increased metabolic demand.

6. The method of claim 5 wherein detecting the reduction in the patient's hemodymanic performance includes detecting a reduction in the patient's average CV-PP during the period in which the pacing rate is increased in response to increased metabolic demand.

7. The method of claim 6 wherein establishing the maximum rate setting includes establishing the maximum rate setting based on the pacing rate corresponding to the reduction in the patient's average CV-PP value.

8. The method of claim 1 wherein the CVP index is a change in a CV-PP, and wherein detecting the reduction in the patient's hemodymanic performance includes identifying a decrease in the CV-PP accompanying the increase in the pacing rate in response to a metabolic demand increase.

9. The method of claim 1 wherein the maximum rate setting is a maximum sensor rate (MSR) or maximum tracking rate (MTR).

10. A method of operating an implanted cardiac rhythm management system in a patient, the method comprising:

acquiring a pressure signal indicative of coronary venous pressure (CVP) from a pressure sensor implanted within the lower apical two thirds of a coronary vein of the patient and deriving a selected CVP index from the pressure signal;

calculating a baseline CVP index value based on the pressure signal, the CVP index based on coronary venous end diastolic pressure (CV-EDP) of the CVP;

applying a pacing stimulus to the patient's heart, the pacing stimulus defined by a set of pacing parameters including a maximum rate setting;

acquiring a signal representative of the patient's metabolic demand from at least one implanted sensor;

responsive to an increase in the patient's metabolic demand, increasing the pacing rate and the maximum rate setting while monitoring the CVP index; and detecting a reduction in the patient's hemodymanic performance based on a change, relative to the CVP index baseline value, in the CVP index resulting from increasing the pacing rate, wherein the change comprises an increase in the slope of the CV-EDP; and maintaining the maximum rate setting at a pacing rate below the pacing rate corresponding to the detected reduction in the patient's hemodynamic performance.

11. The method of claim 10 wherein the baseline CVP index value is derived prior to the pacing rate increase in response to the increase in the patient's metabolic demand.

12. The method of claim 11 wherein the CVP index is a rolling average CV-EDP value during a period in which the pacing rate is increased in response to the increase in the patient's metabolic demand.

13. An implantable rate adaptive cardiac rhythm management system configured for applying pacing stimuli to a patient's heart, the pacing stimuli defined by pacing parameters including a pacing rate and a maximum rate setting, the system comprising:

a plurality of implantable medical electrical leads configured to sense cardiac electrical activity and to deliver the pacing stimuli, at least one of the leads being configured for chronic implantation within a coronary vein of the patient's heart and including a pressure sensor configured to generate a coronary venous pressure (CVP) signal indicative of fluid pressure from within the lower apical two thirds of a coronary vein;

an implantable pulse generator operatively coupled to the leads configured to generate the pacing stimuli, the pulse generator including a control system configured to:

generate a CVP waveform based on the pressure signal and derive a CVP index therefrom, wherein the CVP index is based on coronary venous pulse pressure (CV-PP) sensed by the pressure sensor;

detect reductions in the patient's hemodynamic performance based on the CVP index caused by an increase in the pacing rate; and adaptively adjust the pacing rate and the maximum rate setting in response to changes in the patient's metabolic demand, wherein during use, the maximum rate setting is selectively defined by the control system based on the pacing rate corresponding to the identified reduction in the patient's hemodynamic performance.

* * * * *